(12) United States Patent
Kim et al.

(10) Patent No.: US 12,313,629 B2
(45) Date of Patent: May 27, 2025

(54) STANDARD MATERIAL COMPOSITION FOR VERIFYING BIOANALYZER AND STANDARD STRIP USING SAME

(71) Applicant: BIOSQUARE INC., Seongnam-si (KR)

(72) Inventors: Jung Won Kim, Hwaseong-si (KR); Ho Beom Song, Suwon-si (KR); Sung Wook Yoon, Anyang-si (KR)

(73) Assignee: BIOSQUARE INC., Seongnam-si (KR)

( * ) Notice: Subject to any disclaimer, the term of this patent is extended or adjusted under 35 U.S.C. 154(b) by 875 days.

(21) Appl. No.: 17/439,286

(22) PCT Filed: Mar. 19, 2020

(86) PCT No.: PCT/KR2020/003800
§ 371 (c)(1),
(2) Date: Sep. 14, 2021

(87) PCT Pub. No.: WO2020/190063
PCT Pub. Date: Sep. 24, 2020

(65) Prior Publication Data
US 2022/0155293 A1    May 19, 2022

(30) Foreign Application Priority Data

Mar. 20, 2019   (KR) .................. 10-2019-0031876

(51) Int. Cl.
*B01L 3/00* (2006.01)
*B01F 33/302* (2022.01)
(Continued)

(52) U.S. Cl.
CPC ..... *G01N 33/54388* (2021.08); *G01N 33/582* (2013.01); *G01N 33/587* (2013.01);
(Continued)

(58) Field of Classification Search
CPC .......... G01N 33/54388; G01N 33/582; G01N 33/587; G01N 2496/15; G01N 33/54346;
(Continued)

(56) References Cited

U.S. PATENT DOCUMENTS

| | | | |
|---|---|---|---|
| 2010/0016175 A1 | 1/2010 | Eastman et al. | |
| 2015/0141268 A1 | 5/2015 | Rothberg et al. | |
| 2017/0110625 A1* | 4/2017 | Zhao ................ | C09K 11/08 |

FOREIGN PATENT DOCUMENTS

| | | |
|---|---|---|
| CN | 104880440 A | 9/2015 |
| CN | 106324242 B | 9/2018 |

(Continued)

OTHER PUBLICATIONS

Brulisauer et al.("Homogeneous fluorescent thin films as long-term stable microscopy reference layers." Nanotechnology VIII. vol. 10248. SPIE, 2017). (Year: 2017).*
(Continued)

*Primary Examiner* — Jennifer Wecker
*Assistant Examiner* — Oyeleye Alexander Alabi
(74) *Attorney, Agent, or Firm* — STIP Law Group, LLC

(57) ABSTRACT

The present invention relates to a standard material composition for verifying a bio-analysis equipment, comprising quantum dot-containing nanoparticles. Through a standard strip and/or a standard tray, which are made of the standard material composition, the present invention may increase the analysis accuracy of a bio-analysis equipment.

7 Claims, 10 Drawing Sheets

(51) Int. Cl.
- *B01F 33/3033* (2022.01)
- *B01L 7/00* (2006.01)
- *B01L 9/00* (2006.01)
- *B65G 47/80* (2006.01)
- *B82Y 20/00* (2011.01)
- *B82Y 30/00* (2011.01)
- *B82Y 40/00* (2011.01)
- *C12Q 1/6848* (2018.01)
- *C12Q 1/686* (2018.01)
- *G01N 21/29* (2006.01)
- *G01N 21/65* (2006.01)
- *G01N 33/543* (2006.01)
- *G01N 33/574* (2006.01)
- *G01N 33/58* (2006.01)

(52) U.S. Cl.
CPC ............... *B82Y 20/00* (2013.01); *B82Y 30/00* (2013.01); *B82Y 40/00* (2013.01); *G01N 2496/15* (2013.01)

(58) Field of Classification Search
CPC ........... G01N 33/588; G01N 33/54386; B82Y 20/00; B82Y 30/00; B82Y 40/00
See application file for complete search history.

(56) References Cited

FOREIGN PATENT DOCUMENTS

| KR | 100704011 | B1 |   | 4/2007 |   |
|---|---|---|---|---|---|
| KR | 101327542 | B1 |   | 11/2013 |   |
| KR | 101489195 | B1 |   | 2/2015 |   |
| KR | 20150123189 | A |   | 11/2015 |   |
| KR | 101575396 | B1 | * | 12/2015 |   |
| KR | 20160004524 | A |   | 1/2016 |   |
| KR | 101609618 | B1 |   | 4/2016 |   |
| KR | 20190001742 | A |   | 1/2019 |   |
| KR | 101960616 | B1 |   | 3/2019 |   |
| WO | WO2011008064 | A9 |   | 3/2011 |   |
| WO | WO-2015070700 | A1 | * | 5/2015 | ........... G01N 33/558 |

OTHER PUBLICATIONS

International Search Report of PCT/KR2020/003800, Jun. 30, 2020, English translation.

The extended European search report of EP20 77 3305, Mar. 15, 2023.

Martina Brulisauer et al, Homogeneous fluorescent thin films as long-term stable microscopy reference layers, Nanotechnology, 2017, vol. 10248, 102480P-1-10, SPIE, Bellingham, USA.

A.N. Berlina et al, The Method of Calibration Curves for Immunochromatographic Express Tests. Part 2. Immunochromatographic Express Test With Quantum Dots, Measurement Techniques, Mar. 2013, vol. 55, No. 12, pp. 1434-1441, Springer Science Business Media New York, New York, USA.

Bong-Hyun Jun et al, Ultrasensitive, Biocompatible, Quantum-Dot-Embedded Silica Nanoparticles for Bioimaging, Adv. Funct. Mater, 2012, vol. 22, pp. 1843-1849, Wiley-VCH Verlag Gmbh & Co. KGaA, Weinheim, Germany.

Rae Hyung Kang et al, Systematic Degradation Rate Analysis of Surface-Functionalized Porous Silicon Nanoparticles, Materials, 2019, vol. 12, No. 580, pp. 1-13, MDPI, Basel, Switzerland.

* cited by examiner

[Fig. 1]
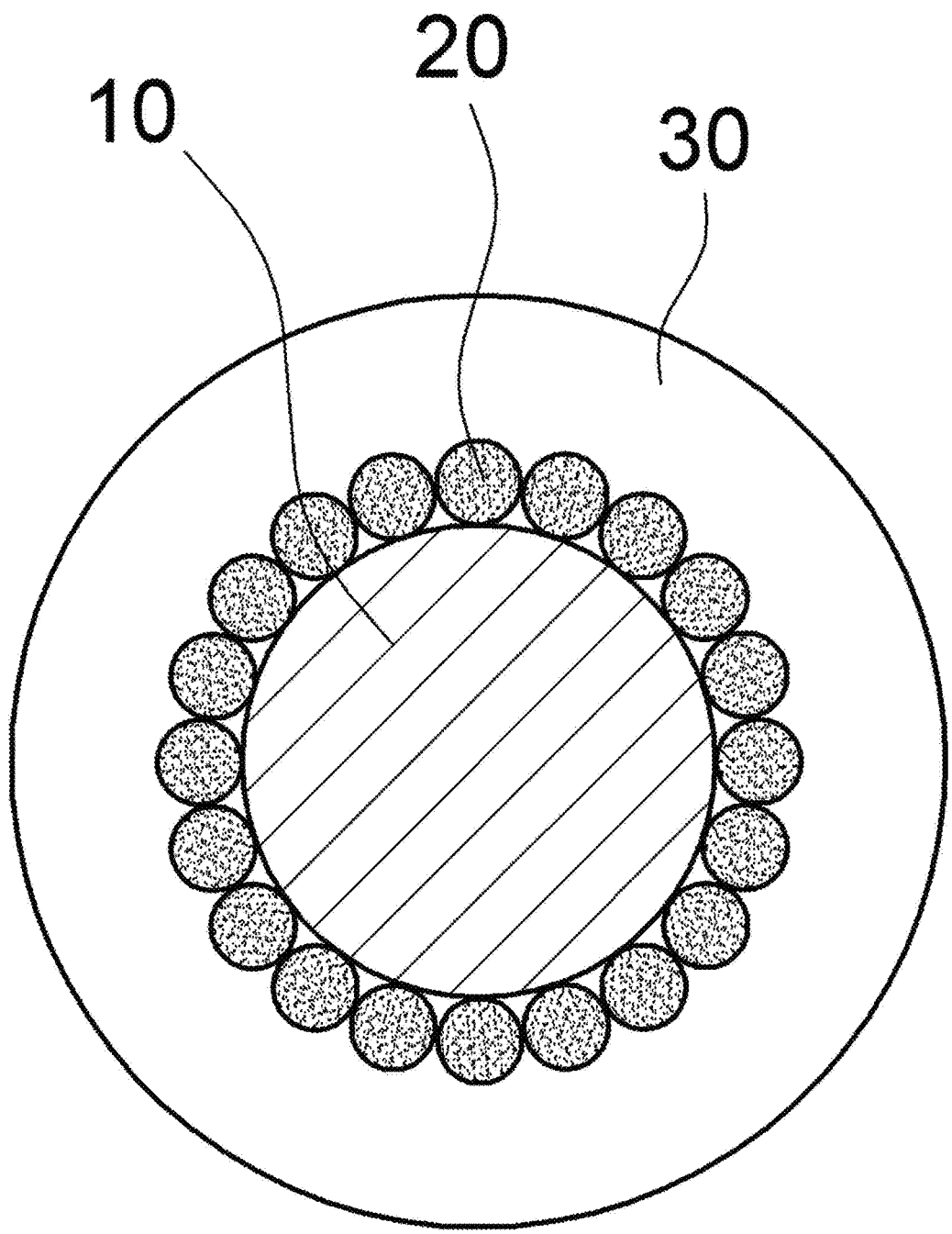

[Fig. 2]
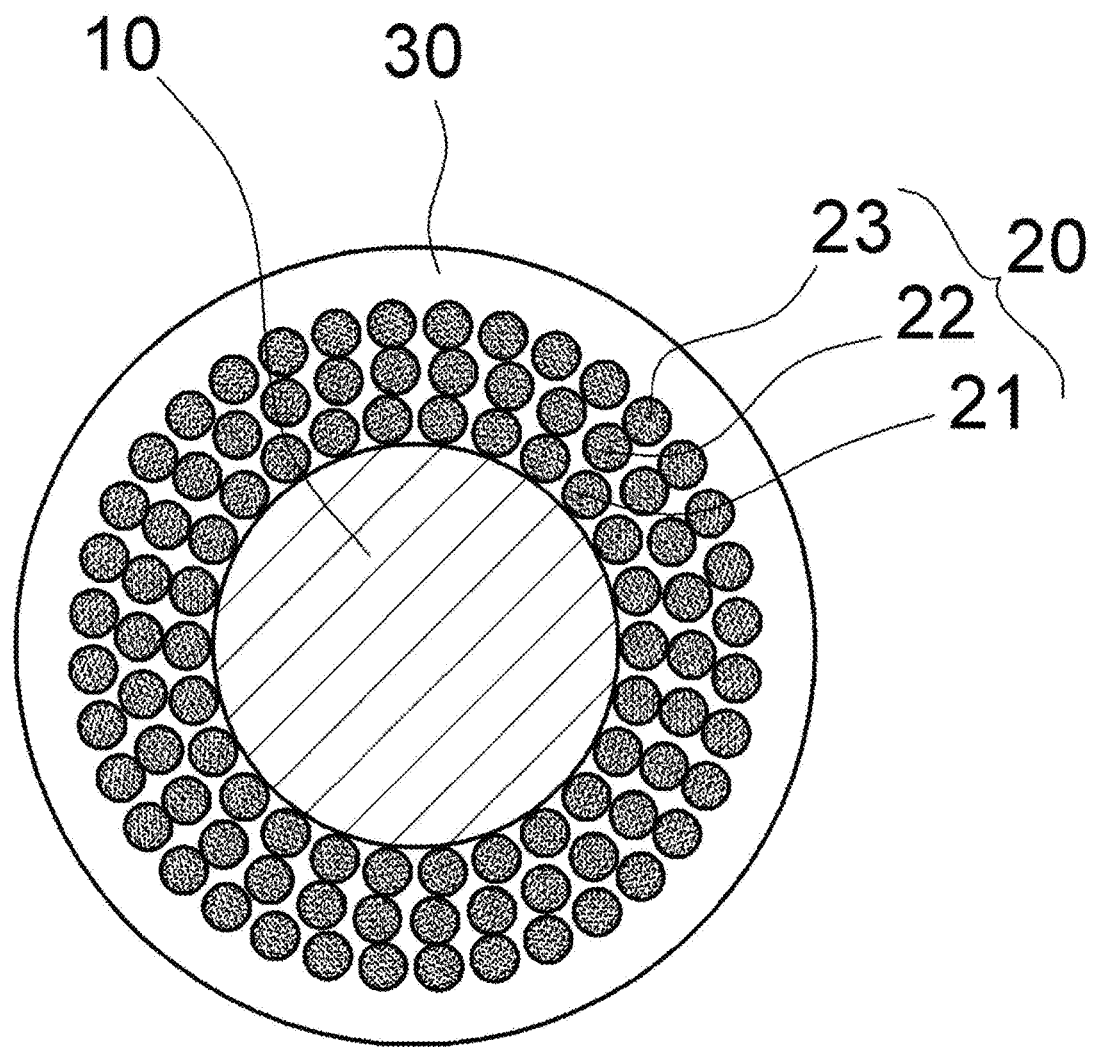

[Fig. 3]
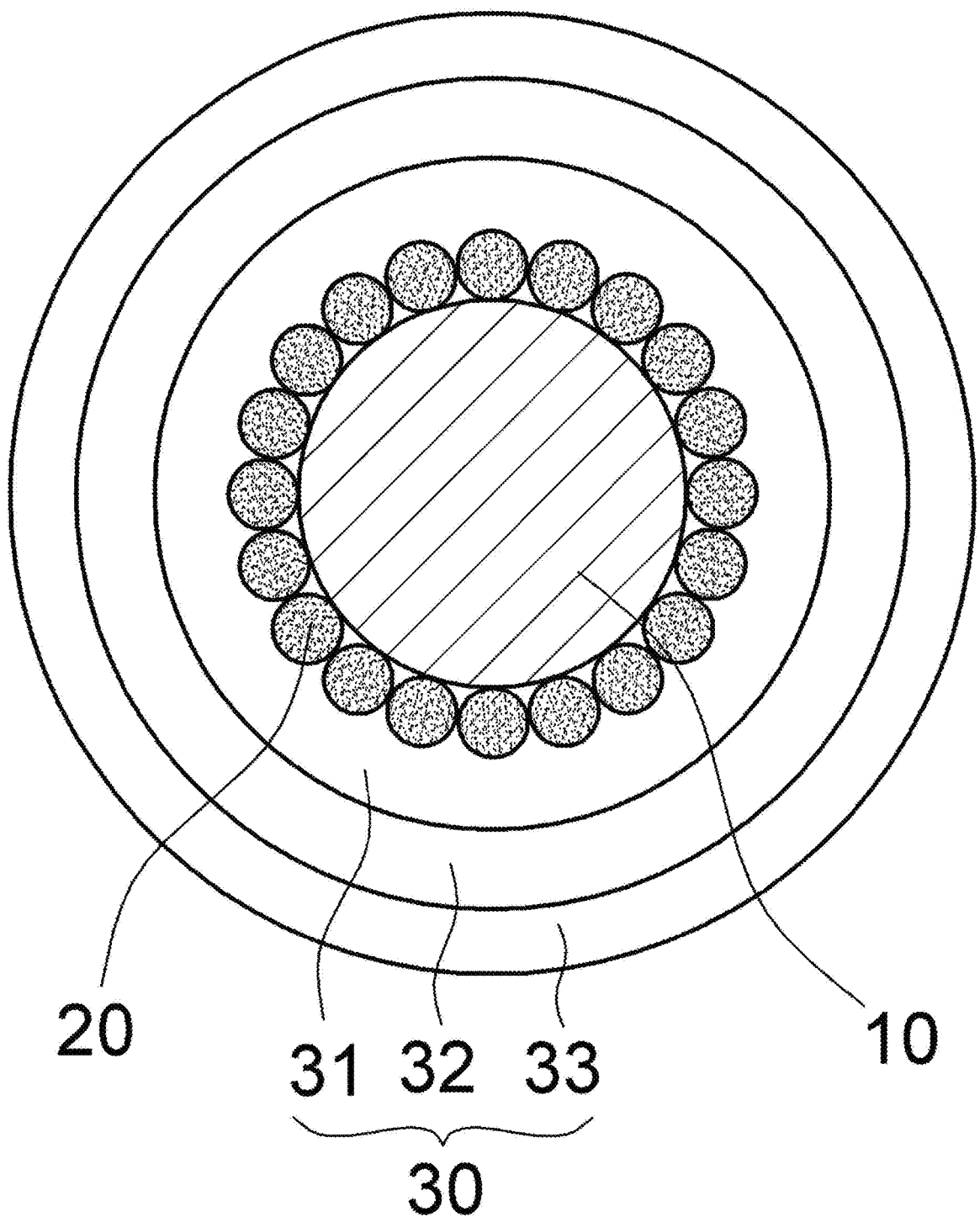

[Fig. 4]
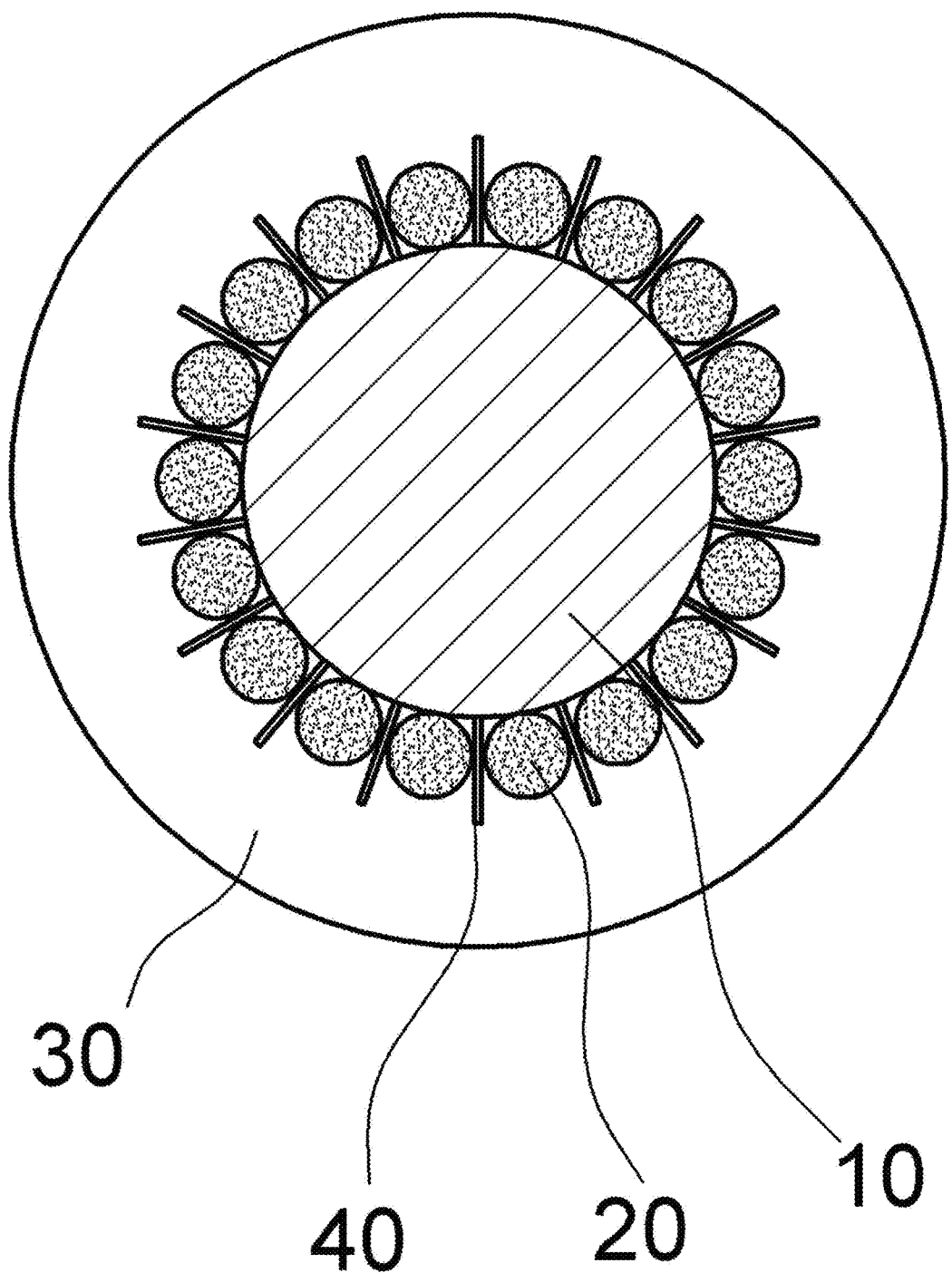
30
40  20  10

[Fig. 5]
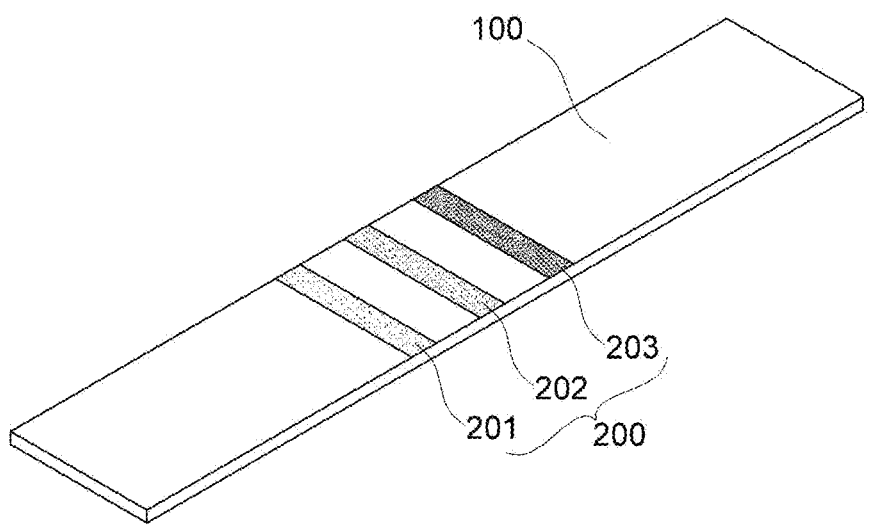

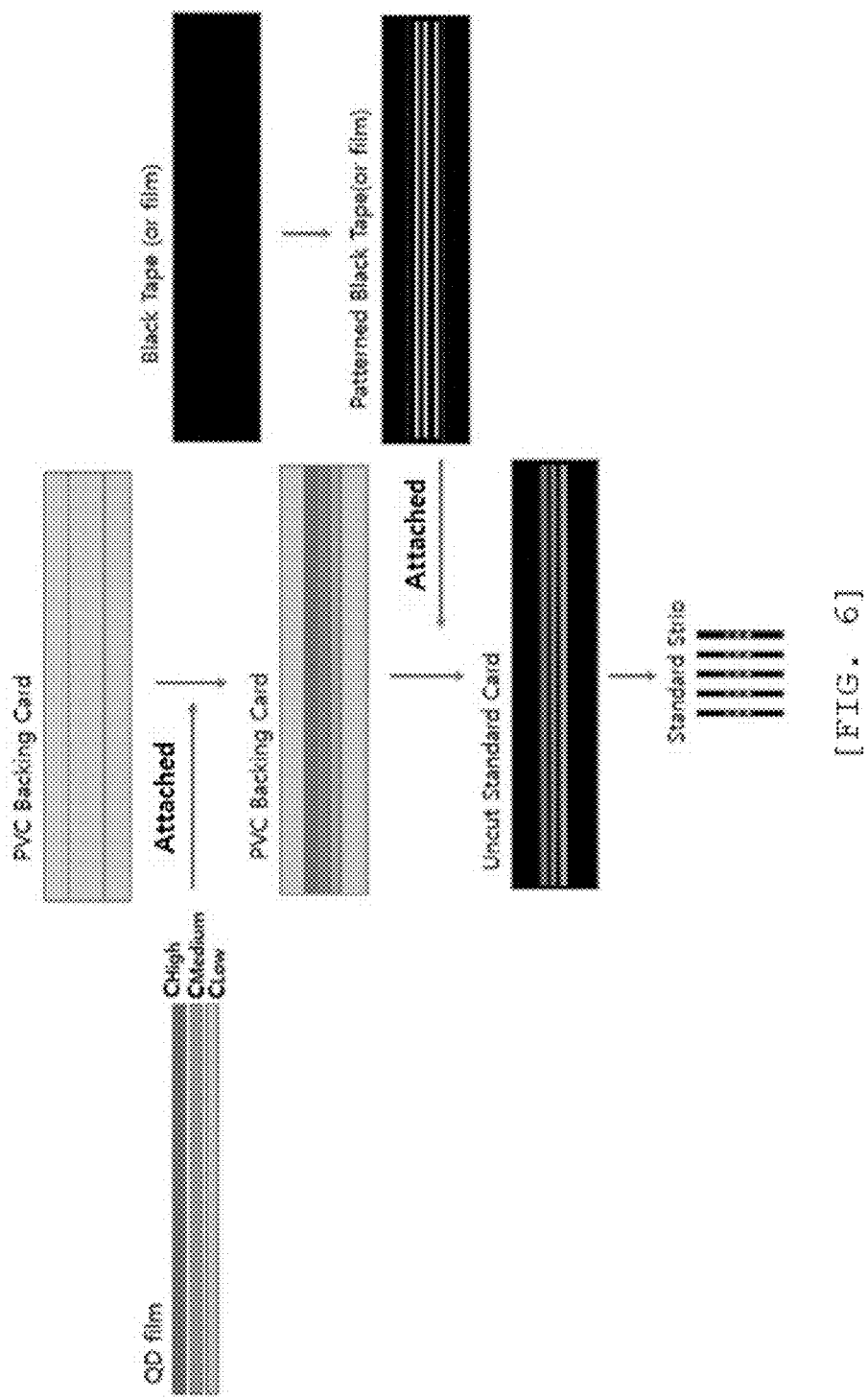
[FIG. 6]

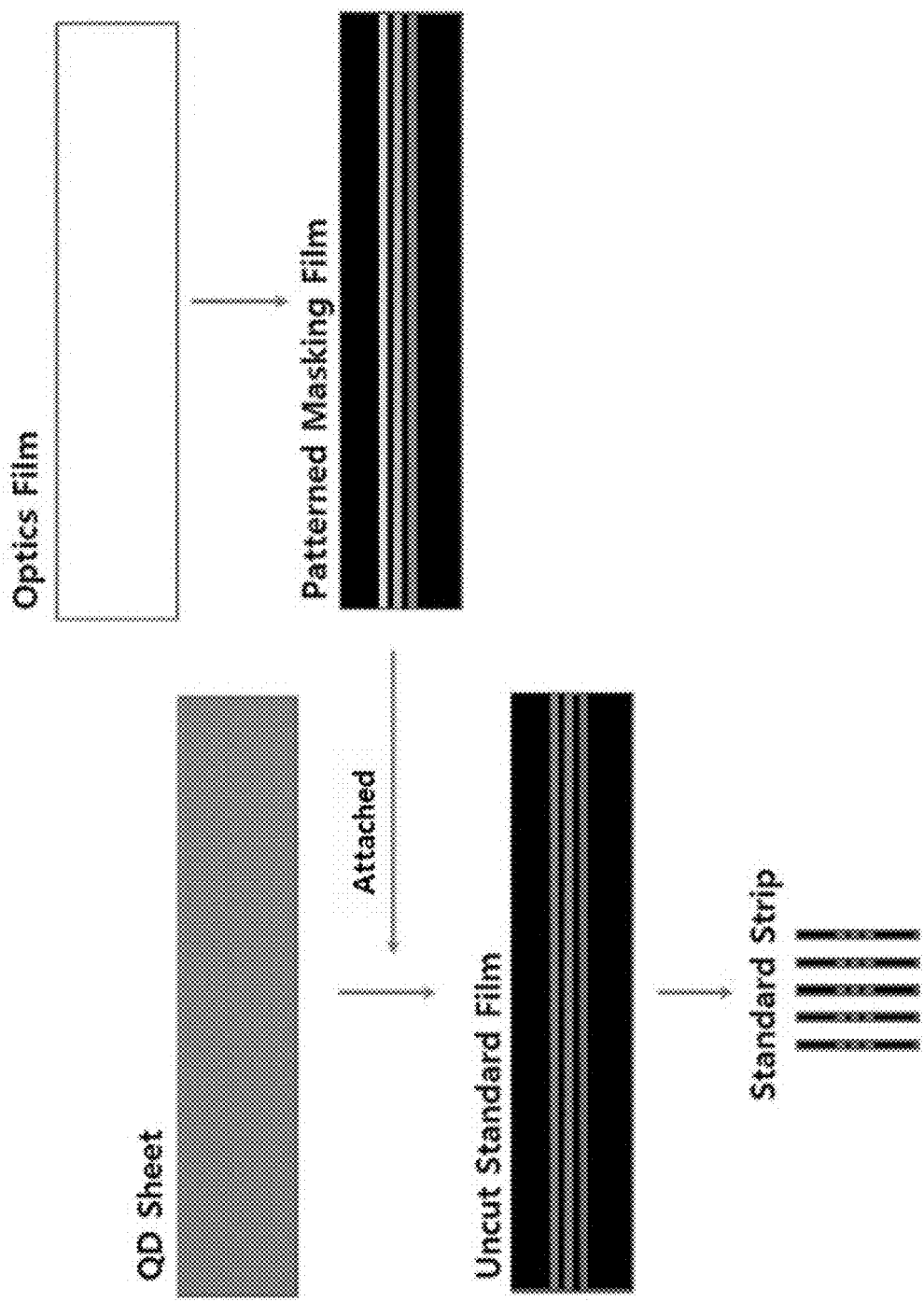
[FIG. 7]

[Fig. 8]
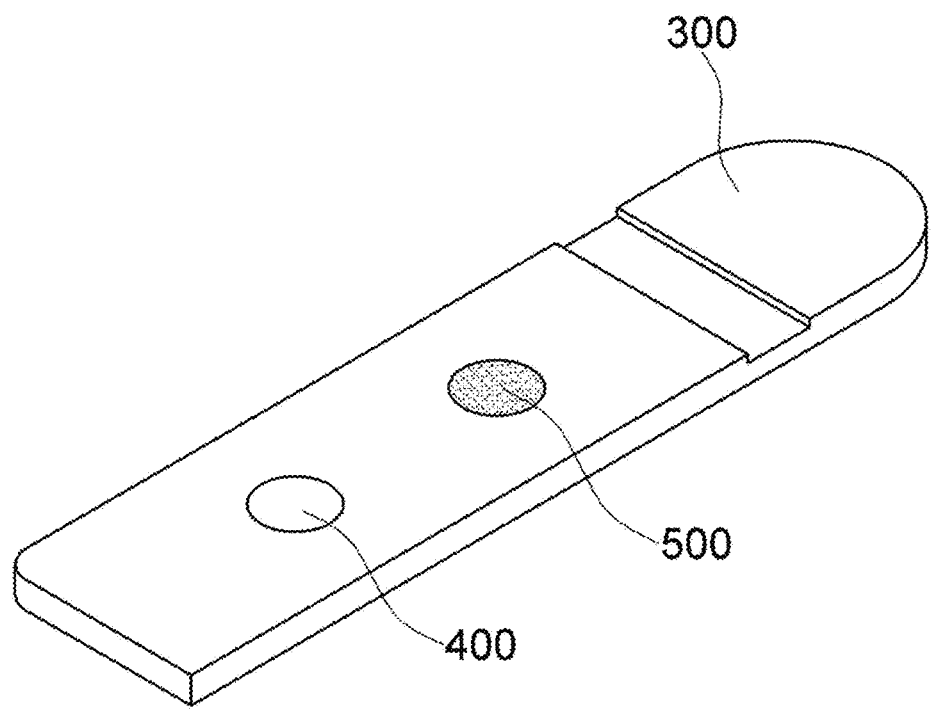
[Fig. 9]
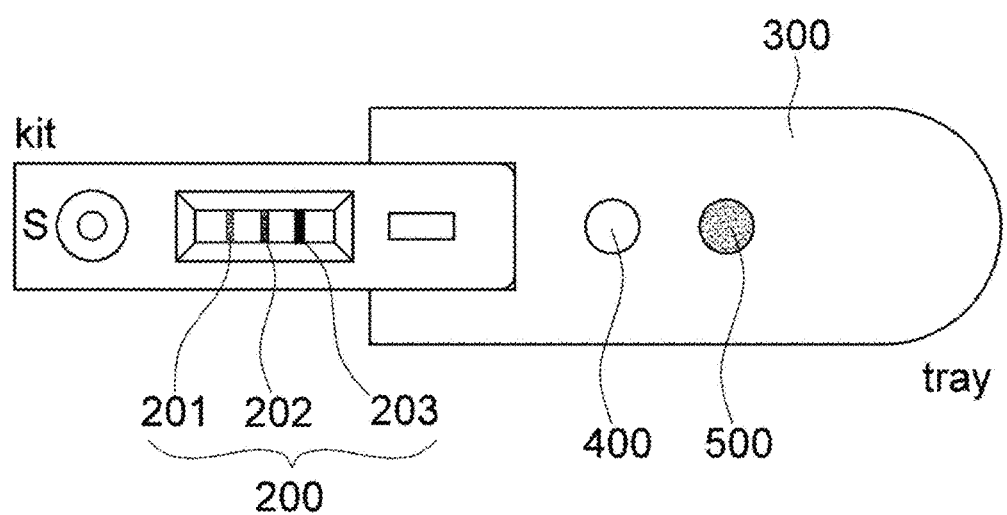

[Fig. 10]
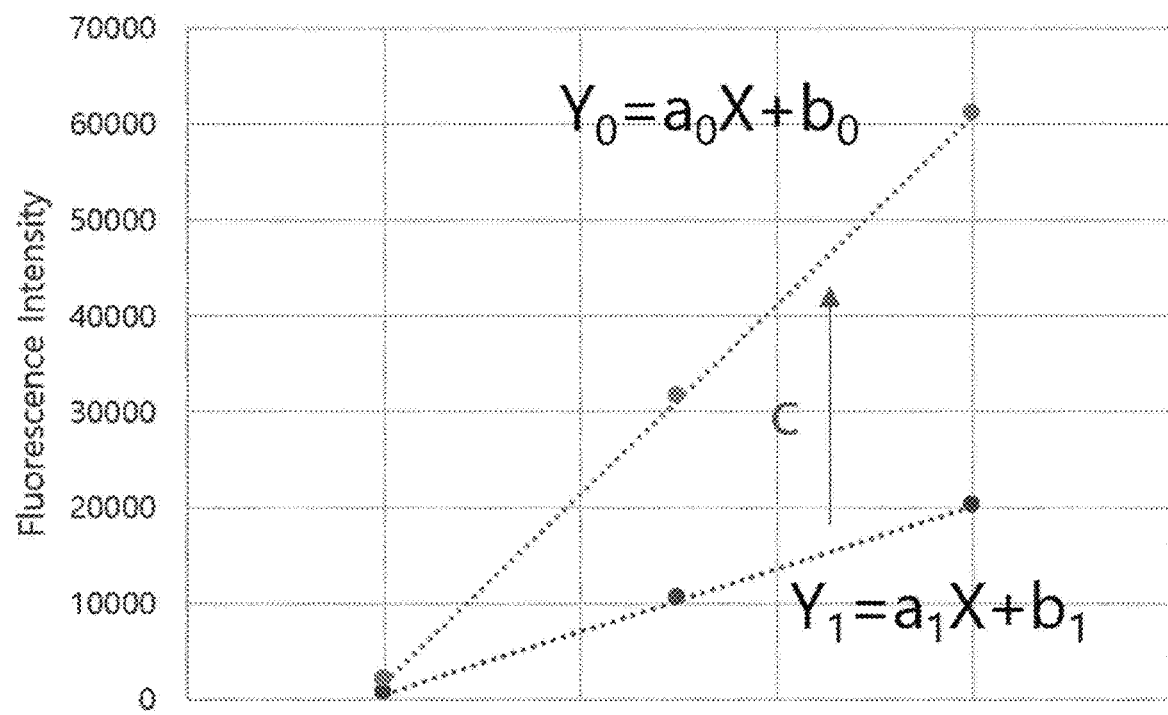

[Fig. 11]
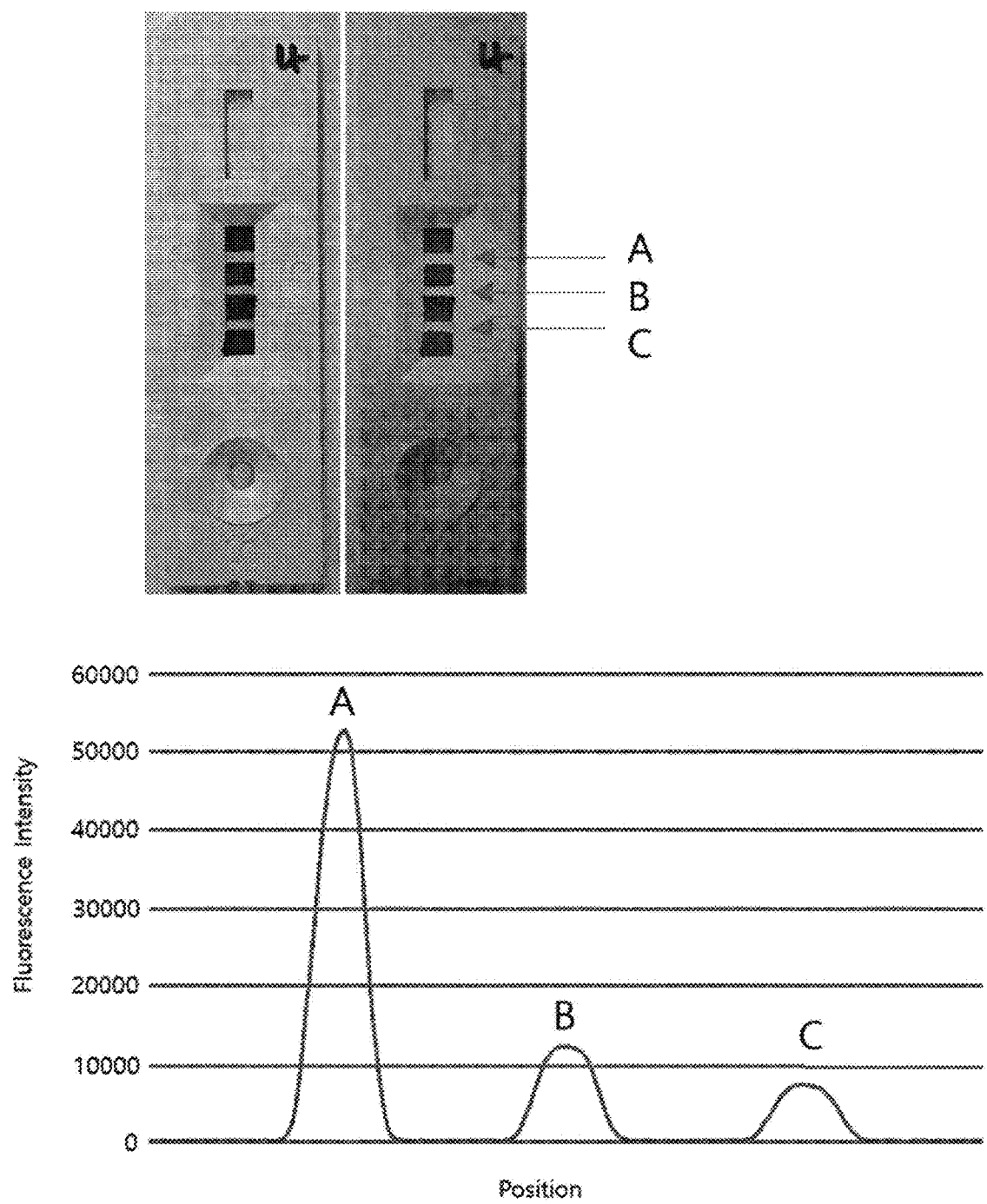

STANDARD MATERIAL COMPOSITION FOR VERIFYING BIOANALYZER AND STANDARD STRIP USING SAME

CROSS-REFERENCE TO RELATED APPLICATIONS

This application is the U.S. National Phase Under 35 U.S.C. § 371 of International Application No. PCT/KR2020/003800 filed on Mar. 19, 2020, which in turn claims the benefit of Korean Application No. 10-2019-0031876 filed on Mar. 20, 2019, the disclosures of which are incorporated by reference into the present application.

TECHNICAL FIELD

The present invention relates to a standard material composition capable of verifying (correcting) the analysis accuracy of a bio-analysis equipment, and a standard strip using the same.

BACKGROUND ART

The optical detection method for measuring the radiant energy transmitted, reflected, and refracted by an object as a function of wavelength is easy to use, accurate, compact or portable, and has the advantages of being able to be used in various reactions at a low price. Accordingly, the optical detection method is applied to various fields such as chemistry, physics, biochemistry, immunology, enzymology, molecular biology, sitology, and the like.

An example of the optical detection method may include a detection (analysis) method in which a lateral flow strip or a microfluidic chip is applied to a bio-analysis equipment equipped with an optical part.

However, in the manufacture of the analysis equipment, although the configuration of the hardware equipped in each analysis equipment is designed to be the same, there is a problem in that a number of analysis equipment manufactured due to various variables such as deviations in electromagnetic characteristics of components and deviations in each configuration combination do not obtain the same data with respect to the identical fluorescence signal. This causes a decrease in the analysis accuracy (reliability) of the results in quantitatively diagnosing and analyzing the detection material by measuring the fluorescence signal intensity.

Therefore, when detection is performed through a number of analysis equipment, a verification process is required to correct the fluorescence intensity deviation of the analysis equipment using a standard material as a reference to indicate the required fluorescence signal intensity. Accordingly, in the prior art, a verification process of analysis equipment has been performed by using a mixed ink with gold, latex, or the like, or a fluorescent substance such as europium as a standard material.

However, the ink has problems in that since it is manufactured as a standard material through a printing process based on the color diagram, an error in color expression occurs whenever the printing process is performed, and since it is easily contaminated when exposed to the outside, its lifespan is not long. In addition, the fluorescent substance has problems in that since the photobleaching phenomenon occurs during the manufacturing process of the standard material or it is sensitive to changes in light, temperature, or humidity, its reproducibility is poor.

Accordingly, there is a demand for the development of an improved standard material in order to increase the analysis accuracy of the bio-analysis equipment.

DISCLOSURE

Technical Problem

An object of the present invention is to provide a standard material composition for verifying a bio-analysis equipment that may verify (correct) the analysis accuracy of the bio-analysis equipment.

It is another object of the present invention to provide a standard strip prepared from the standard material composition.

It is another object of the present invention to provide a standard tray prepared from the standard material composition.

It is another object of the present invention to provide a method of verifying a bio-analysis equipment using the standard strip and/or the standard tray.

Technical Solution

In order to achieve the above objects, the present invention provides a standard material composition for verifying a bio-analysis equipment, comprising quantum dot-containing nanoparticles.

The quantum dot-containing nanoparticle may include a core part; a quantum dot part bound to the surface of the core part; and a shell part for protecting the core part and the quantum dot part.

The quantum dot part may include a plurality of quantum dot-embedded layers.

The shell part may include a plurality of silica shell layers.

The quantum dot-containing nanoparticle may further include a support part for supporting the binding of the core part and the shell part.

Meanwhile, the present invention provides a standard strip comprising one or more luminescence lines formed of the standard material composition for verifying a bio-analysis equipment.

The luminescence line may be equipped in plurality and the concentration of quantum dots may be different between a plurality of luminescence lines.

The luminescence line may be equipped in plurality and the fluorescence signal intensity may be different between a plurality of luminescence lines.

In addition, the present invention provides a standard tray comprising a luminescence part formed of the standard material composition for verifying a bio-analysis equipment.

In addition, the present invention provides a method of verifying a bio-analysis equipment, comprising the steps of: irradiating a light source to a standard tray comprising a luminescence part formed of the standard material composition for verifying a bio-analysis equipment; determining whether the fluorescence intensity value of the luminescence part emitted by the irradiated light source falls within a range of standard fluorescence intensity values input to an optical part of the bio-analysis equipment; and first correcting the range of the standard fluorescence intensity values input to the optical part so that the fluorescence intensity value falls within the range of the standard fluorescence intensity values by the determination.

The method of verifying a bio-analysis equipment of the present invention may further comprise the step of secondarily correcting the standard fluorescence intensity values input to the optical part through the standard strip comprising one or more luminescence lines formed of the standard material composition for verifying a bio-analysis equipment.

Advantageous Effects

According to the present invention, the analysis accuracy of a bio-analysis equipment may be increased by performing the correction of the optical part in a bio-analysis equipment using the standard strip and/or the standard tray prepared from the standard material composition comprising quantum dot-containing nanoparticles. Therefore, the present invention may contribute to providing reliable biodetection (analysis) results.

DESCRIPTION OF DRAWINGS

FIG. 1, FIG. 2, FIG. 3 and FIG. 4 are cross-sectional views showing the quantum dot-containing nanoparticles according to the present invention.

FIG. 5 is a perspective view showing the standard strip according to the present invention.

FIG. 6 and FIG. 7 are flowcharts showing the process of preparing the standard strip according to the present invention.

FIG. 8 is a perspective view showing the standard tray according to the present invention.

FIG. 9 is a schematic view showing the standard assembly according to the present invention.

FIG. 10 is a reference view for explaining the process of verifying the bio-analysis equipment according to the present invention.

FIG. 11 is a reference view for explaining Experimental Example 1 according to the present invention.

BEST MODE

The terms and words as used in the description and claims of the present invention should not be construed as limited to conventional or dictionary meanings, but should be construed as the meaning and concept consistent with the technical idea of the present invention based on the principle that the inventor can appropriately define the concept of the terms to describe its own invention in the best way.

The present invention is intended to provide a standard material having an improved lifespan while increasing the analysis accuracy of a bio-analysis equipment, by introducing quantum dots that have little photobleaching phenomenon and are not sensitive to changes in light, temperature, or humidity into a standard material for the verification (correction) of the bio-analysis equipment, and the present invention will be described in detail with reference to the drawings as follows.

The present invention provides a standard material composition for verifying a bio-analysis equipment, comprising quantum dot-containing nanoparticles (hereinafter referred to as a "standard material composition"). The standard material composition according to the present invention may be defined as a composition that is used to verify (correct) a bio-analysis equipment so that the bio-analysis equipment can indicate the correct detection values (analysis values) before detecting (analyzing) the bio-sample (biological sample) with the bio-analysis equipment.

The quantum dot-containing nanoparticles comprised in the standard material composition according to the present invention may not be particularly limited as long as they contain quantum dots. That is, the quantum dot-containing nanoparticles may be composed of only quantum dot particles, or a combination of quantum dot particles and other components. At this time, the quantum dot in the present invention is a semiconductor material, and may be defined as a material in which atoms form a spherical layer with about 5 to 10 layers and the radius is usually 10 nm or less, and that exhibits a quantum confinement effect in which a luminous wavelength differs from that of a bulk state since the electron motion characteristics in the semiconductor material in the bulk state become further restricted when it becomes small to a certain size or less. If this quantum dot reaches the energy excited state by receiving light from an excitation source, it may exhibit luminescent properties that autonomously emits energy according to a corresponding energy band gap.

The quantum dot-containing nanoparticle of the present invention may be specifically a quantum dot particle themselves or a quantum dot-containing nanoparticle including a core part 10, a quantum dot part 20, and a shell part 30 as shown in FIG. 1. The quantum dot-containing nanoparticle including the core part 10, the quantum dot part 20, and the shell part 30 will be described in detail as follows.

The core part 10 included in the quantum dot-containing nanoparticle of the present invention may include an organic particle or inorganic particle. The inorganic particle may be specifically one consisting of one or more components selected from the group consisting of silica, alumina, titanium dioxide, and zinc dioxide. Since these inorganic particles have high stability, when they are applied to the core part 10, the size of the quantum dot-containing nanoparticles as well as the size of the core part 10 may be easily controlled, and due to these, quantum dot-containing nanoparticles having excellent optical properties (luminescent properties) while having various particle sizes may be obtained.

The diameter of the core part 10 may be 10 to 100,000 nm, specifically 80 to 1,000 nm. As the diameter of the core part 10 is within the above range, handling and further post-processing of quantum dot-containing nanoparticles may be easily made.

The quantum dot part 20 included in the quantum dot-containing nanoparticle of the present invention is bonded to the surface of the core part 10, and may serve to enable the quantum dot-containing nanoparticle to exhibit optical properties. Specifically, the quantum dot part 20 may have a structure (a single quantum dot-embedded layer) in which a plurality of quantum dots surround the entire surface of the core part 10. In addition, the quantum dots included in the quantum dot part 20 may form a cross-linkage with silica, which is a component of the shell part 30, and a structure in which quantum dots are randomly or uniformly bonded to the silica that is the component of the shell part 30 through the cross-linking may appear.

As an example, the quantum dots of the quantum dot part 20 may be uniformly dispersed and bonded to the surface of the core part 10 through the process of being modified with a material having functional groups at both ends, and due to this, the quantum dot part 20 may be formed. The material having functional groups at both ends may be specifically one to which a functional group including one or more atoms selected from the group consisting of sulfur, nitrogen, and phosphorus at one end, and one or more functional groups selected from the group consisting of a silane group, an amino group, a sulfone group, a carboxyl group, and a hydroxy group at the other end are bonded. Specifically, the material having functional groups at both terminals may be mercaptopropyltrimethoxysilane, mercaptomethyldiethoxysilane, mercaptopropylmethyldimethoxysilane, or mercaptopropyltriethoxysilane.

On the one hand, the quantum dots included in the quantum dot part 20 may have a single core structure composed of a Group II-VI series semiconductor component, a Group III-V series semiconductor component, or a Group IV-IV series semiconductor component, or may have a structure in which a coating layer is formed by coating a Group II-IV series semiconductor component on a single core. This may also be applied to the above-described quantum dot particles.

The Group II-VI series semiconductor may be one to which at least one Group IIB element on the periodic table and at least one Group VIB element are bonded. Specifically, the Group II-VI series semiconductor may be selected from the group consisting of CdS, CdSe, CdTe, ZnSe, ZnS, PbS, PbSe, HgS, HgSe, HgTe, CdHgTe, and $CdSe_xTe_{1-X}$. The Group III-V series semiconductor may be specifically selected from the group consisting of GaAs, InAs, and InP.

Herein, it may be more preferable in terms of luminous efficiency that the quantum dots have a structure in which a coating layer is formed on a single core rather than a single core structure. This is because the coating layer acts as a passivation layer to protect the single core, thereby increasing the stability of the quantum dots. Specifically, as the quantum dots, one in which a coating layer made of ZnS is formed on a single core made of CdSe or CdS, or one in which a coating layer made of CdSe or ZnSe is formed on a single core structure made of CdSe (Type 1 quantum dots) may be used.

In addition, as the quantum dots, one in which a hydrophobic organic compound (e.g. oleic acid) is coated on the quantum dots having a single core structure or a structure in which a coating layer is formed on a single core may be used.

The diameter of these quantum dots may be 1 to 50 nm, specifically 1 to 20 nm. In addition, when the quantum dots have a structure in which a coating layer is formed on a single core, the diameter of the single core may be 1 to 20 nm, specifically 2 to 10 nm.

The quantum dot part 20 including the quantum dots may include a plurality of quantum dot-embedded layers (quantum dot-coating layers) 21, 22, 23 as shown in FIG. 2. Specifically, the quantum dot part 20 may include a first quantum dot-embedded layer 21 surrounding the surface of the core part 10, a second quantum dot-embedded layer 22 surrounding the first quantum dot-embedded layer 21, and a third quantum dot-embedded layer 23 surrounding the second quantum dot-embedded layer 22. Herein, the number of quantum dot-embedded layers 21, 22, and 23 is not limited to that shown in FIG. 2, and may be adjusted according to the required physical properties and size of quantum dot-containing nanoparticle. In this way, when the quantum dot part 20 includes a plurality of quantum dot-embedded layers 21, 22, 23, the quantum dot-containing nanoparticle includes multi-layered multi-quantum dots, thereby exhibiting high luminous efficiency (quantum yield) and improved brightness. This may lead to improving the optical properties (luminescent properties) of the standard material composition according to the present invention.

The shell part 30 included in the quantum dot-containing nanoparticle of the present invention is bonded to surround the quantum dot part 20, and may serve to protect the core part 10 and the quantum dot part 20. The shell part 30 may be mainly made of silica.

The thickness of the shell part 30 may be 1 to 1,000 nm, specifically 1 to 300 nm. As the thickness of the shell part 30 is within the above range, it is possible to prevent the quantum dot-containing nanoparticle from becoming excessively heavy while protecting the core part 10 and the quantum dot part 20, thereby increasing the applicability of the quantum dot-containing nanoparticle.

Such a shell part 30 may include a plurality of silica shell layers 31, 32, 33 as shown in FIG. 3. Specifically, the shell part 30 may include a first silica shell layer 31 surrounding the quantum dot part 20, a second silica shell layer surrounding the first silica shell layer 31, and a third silica shell layer 33 surrounding the second silica shell layer 32. Herein, the number of silica shell layers 31, 32, and 33 is not limited to that shown in FIG. 3, and may be adjusted according to the required physical properties and size of quantum dot-containing nanoparticle. In this way, when the shell part 30 includes a plurality of silica shell layers 31, 32, 33, the capping density of the shell part 30 become higher to increase the stability of the quantum dot-containing nanoparticle. In addition, by adjusting the number of the silica shell layers 31, 32, 33, the size of the quantum dot-containing nanoparticle may be freely controlled to a required level. At this time, the size control of the nanoparticle may also be embodied by controlling the thickness by adjusting the volume of the reaction material upon the formation of the shell part 30 in addition to adjusting the number of silica shell layers 31, 32, 33 included in the shell part 30.

On the one hand, the ratio (a:b, length ratio) of (a) the diameter of the core part 10 and (b) the thickness of the shell part 30 may be 120 to 3:1 to 7.5, specifically 6 to 3:1 to 2. As the ratio of the diameter of the core part 10 to the thickness of the shell part 30 is within the above range, the optical properties and stability of the quantum dot-containing nanoparticle may be improved.

Such a quantum dot-containing nanoparticle may further include the support part 40 that is bonded to each of the core part 10 and the shell part 30 to support the binding of the core part 10 and the shell part 30. That is, referring to FIG. 4, the quantum dot-containing nanoparticle further includes a support part 40 having a bridge structure connecting between the core part 10 and the shell part 30. When such a support part 40 is further included, the bonding density (cross-linking density) of the core part 10 and the shell part 30 increases, so that the stability of the quantum dot-containing nanoparticle may be higher, and due to this, the quantum dot-containing nanoparticle having excellent optical properties may be provided. This may lead to improving the optical properties (luminescent properties) of the standard material composition according to the present invention.

The support part 40 may be formed of a carbon supporter having a first functional group bonded to the core part 10 at one end and having a second functional group bonded to the shell part 30 at the other end. Herein, the first functional group may be selected from the group consisting of a nitro group, an imide group, an ester group, a maleimide group, an iodoacetamide group, an N-hydroxysuccinimide group, and a tosyl group. In addition, the second functional group may be selected from the group consisting of a trimethoxysilane group, a triethoxysilane group, a dimethoxysilane group, a diethoxysilane group, a methoxysilane group, and an ethoxysilane group.

Specifically, the carbon supporter may be one in which oligoethylene glycol or polyethylene glycol forms a main skeleton structure, wherein the first functional group is bonded to one end of the main skeleton structure, and the second functional group is bonded to the other end of the main skeleton structure. In addition, the carbon supporter may have a molecular weight of 100 to 15,000 g/mol. When the carbon supporter has a main skeleton structure such as oligoethylene glycol or polyethylene glycol, dispersibility in a solvent (e.g. ethanol) may be increased in the process of preparing quantum dot-containing nanoparticles, and due to this, quantum dot-containing nanoparticles having improved binding density (cross-linking density) and stability may be provided.

These quantum dot-containing nanoparticles may be comprised in the standard material composition in an amount of 1 to 80 parts by weight, specifically 1 to 40 parts by weight, based on 100 parts by weight of the standard material composition, when considering the optical properties, workability, moldability, and the like of the standard material composition.

On the one hand, the standard material composition according to the present invention may further comprise a binder resin, a curing agent, an additive, and a solvent to be molded into various shapes.

The binder resin further comprised in the standard material composition according to the present invention may not be particularly limited as long as it is a resin used in the field of optical materials. Specifically, the binder resin may be one or more selected from the group consisting of an acrylate-based resin, a polyester-based resin, a polyamide-based resin, a polyimide-based resin, a polycarbonate-based resin, and a silicone-based resin.

Such a binder resin may be comprised in the standard material composition in an amount of 10 to 50 parts by weight, specifically 25 to 50 parts by weight, based on 100 parts by weight of the standard material composition, when considering the workability, moldability, dispersibility, and the like of the standard material composition.

The curing agent further comprised in the standard material composition according to the present invention may not be particularly limited as long as it causes a curing reaction of the binder resin. Specifically, the curing agent may be one or more selected from the group consisting of an oxazoline-based curing agent, a polyisocyanate-based curing agent, a melamine-based curing agent, and a carbodiimide-based curing agent.

These curing agents may be comprised in the standard material composition in an amount of 1 to 10 parts by weight, specifically 1 to 5 parts by weight, based on 100 parts by weight of the standard material composition, when considering the curability, workability, and the like of the standard material composition.

The additive further comprised in the standard material composition according to the present invention may not be particularly limited as long as it is an additive used in the field of optical materials. Specifically, the additive may be one or more selected from the group consisting of an inorganic filler, a leveling agent, an antifoaming agent, a dispersion stabilizer, a viscosity controlling agent, an antioxidant, and a heat-resistant stabilizer.

These additives may be comprised in the standard material composition in an amount of 5 to 50 parts by weight, specifically 20 to 50 parts by weight, based on 100 parts by weight of the standard material composition, when considering the workability, optical properties, and the like of the standard material composition.

The solvent further comprised in the standard material composition according to the present invention may not be particularly limited as long as it is a solvent used in the field of optical materials. Specifically, the solvent may be one or more selected from the group consisting of an aromatic hydrocarbon-based solvent such as benzene, toluene, xylene, and ethylbenzene; an aliphatic hydrocarbon-based solvent such as pentane, hexane, and heptane; an alcohol-based solvent such as methanol, ethanol, propanol, isopropanol, cyclohexanol, benzyl alcohol, octanol, ethylene glycol, propylene glycol, and glycerol; a ketone-based solvent such as acetone, methyl ethyl ketone, diisobutyl ketone, and methyl amyl ketone; an ester-based solvent such as ethyl acetate, isopropyl acetate, butyl acetate, and ethylacetoacetate; and an ether-based solvent such as ethyl ether, butyl ether, tetrahydrofuran, and the like.

These solvents may be comprised in the standard material composition in an amount of 1 to 50 parts by weight, specifically 10 to 20 parts by weight, based on 100 parts by weight of the standard material composition, when considering the workability, moldability, and the like of the standard material composition.

The above-described standard material composition according to the present invention may be applied to verification (correction) of a bio-analysis equipment through a process of curing and molding according to a verification device. Specifically, the present invention provides a standard strip, a standard tray, or a standard assembly as the verification device, and these will be described in detail as follows.

The present invention provides a standard strip comprising one or more luminescence lines formed of the above-described standard material composition. Specifically, referring to FIG. 5, the standard strip according to the present invention may comprise a strip body part 100; and one or more luminescence lines 200.

The strip body part 100 included in the standard strip according to the present invention may be made of materials and structures commonly used in the field of biostrips.

The luminescence line 200 included in the standard strip according to the present invention is formed of the above-described standard material composition, and may be equipped in one or a plurality on the strip body part 100. The luminescence line 200 includes the above-described quantum dot-containing nanoparticles, so that light may be emitted by the light source.

Specifically, as shown in FIG. 5, the luminescence line 200 may be equipped in plurality with a first luminescence line 201, a second luminescence line 202, and a third luminescence line 203, and in this case, concentrations of quantum dots between each luminescence line may be different from each other. That is, when each luminescence line is formed, standard material compositions having different contents of quantum dots (quantum dot-containing nanoparticles) are respectively applied to form luminescence lines having different concentrations of quantum dots. As an example, a plurality of luminescence lines 201, 202, 203 may be formed by setting (adjusting) the concentration (content) of the quantum dots of each standard material composition so that the concentration of quantum dots in the first luminescence line 201 is low ($C_{low}$), the concentration of quantum dots in the second luminescence line 202 is higher than that contained in the first luminescence line 201 ($C_{low} < C_{medium}$) and the concentration of quantum dots in the third luminescence line 203 is higher than that contained in the second luminescence line 202 ($C_{low} < C_{medium} < C_{high}$).

In addition, the luminescence line 200 may be equipped in plurality, and the fluorescence signal intensity may be different between each of the luminescence lines 201, 202, and 203. That is, the plurality of luminescence lines 201, 202, and 203 exhibiting different fluorescence intensities may be formed by controlling the transmission process (transmittance) of the fluorescence signal emitted from each of the luminescence lines 201, 202, and 203.

Herein, the number of luminescence lines 200 is not limited to that shown in FIG. 5, and may be appropriately adjusted according to analysis conditions.

In this way, the standard strip according to the present invention has a quantum dot concentration gradient or is equipped with a plurality of luminescence lines 201, 202, and 203 having different fluorescence signal intensities, so that the error (deviation) of the analysis equipment may be corrected more precisely in the process of verifying the bio-analysis equipment, and due to this, the analysis accuracy of the bio-analysis equipment may be increased.

This standard strip according to the present invention may be prepared through the process as shown in FIG. 6 or 7.

Specifically, as shown in FIG. 6, each of standard material compositions having different contents of quantum dots (or quantum dot-containing nanoparticles) is applied (coated) on a conventional optical film (Optics film), covered with a cover film, and then subjected to a curing process to prepare a plurality of QD films (for example, three QD films having concentrations of $C_{low}$, $C_{medium}$, and $C_{high}$) having a quantum dot concentration gradient, and each prepared QD film is attached to the PVC Backing Card according to the line position of the PVC Backing Card, and then the patterned Black Tape (or film) is placed and attached on the PVC Backing Card to expose the QD film line to prepare an uncut Standard Card, and then the Standard Card is cut to the required size to prepare the standard strip according to the present invention.

In addition, as shown in FIG. 7, a QD sheet made of the standard material composition is prepared, one surface of the optical film is patterned by a printing method to prepare a masking film in which lines having different light transmittance are formed, and then the prepared QD sheet is covered with the prepared masking film and cured to prepare an uncut standard card, and then the standard card is cut to a required size to prepare a standard strip according to the present invention.

Since the standard strip according to the present invention comprises the luminescence line 200 formed of the above-described standard material composition, it may be conveniently used for verification (correction) of the bio-analysis equipment and the analysis accuracy of the bio-analysis equipment may be increased. In addition, the photobleaching phenomenon does not occur well in the quality control process during the preparing of standard strips, and stable performance may be realized even if the storage environment (light shielding, temperature, humidity, and the like) changes. In addition, since the standard strip is prepared using an optical film, UV exposure and external contamination are prevented, so that a long service life may be secured.

The present invention provides a standard tray comprising a luminescence part formed of the above-described standard material composition. Specifically, referring to FIG. 8, the standard tray according to the present invention may include a tray body part 300; reference part 400; and a luminescence part 500. Herein, the standard tray according to the present invention may be a tray serving to mount a bio kit equipped with a bio strip.

The tray body part 300 comprised in the standard tray according to the present invention may be made of materials and structures commonly used in the field of bio-trays.

The reference part 400 comprised in the standard tray according to the present invention serves to provide a reference point in analyzing the fluorescence signal of the luminescence part 500, and may be made of a commonly used material.

The luminescence part 500 comprised in the standard tray according to the present invention may be formed of the above-described standard material composition to emit light by a light source. This luminescence part 500 may be formed through a process of curing the above-described standard material composition into a paste state.

Since the standard tray according to the present invention comprises the luminescence part 500 formed of the above-described standard material composition, it may be conveniently used for verification (correction) of the bio-analysis equipment and the analysis accuracy of the bio-analysis equipment may be increased.

The present invention provides a standard assembly in which the above-described standard strip and standard tray are combined. That is, referring to FIG. 9, the present invention may provide a standard assembly comprising a standard kit equipped with the above-described standard strip and the above-described standard tray on which the standard kit is mounted. This standard assembly may be efficiently used for first and secondary correction of a bio-analysis equipment to be described later.

On the one hand, the present invention provides a method of verifying a bio-analysis equipment using the above-described standard strip and/or standard tray, and this will be described in detail as follows. Herein, the verification of the bio-analysis equipment according to the present invention may be made before preforming the analysis of the bio-sample (e.g. antigen, receptor, virus, enzyme, infectious immunoglobulin, cytokine, or other infectious factors) with the bio-analysis equipment. In addition, the fluorescence intensity of the part except the luminescence part 500 of the standard tray or the luminescence line 200 of the standard strip is defined as a background value, and verification and analysis may be performed with a value obtained by subtracting the background value from the fluorescence intensity value of the luminescence part 500 or the luminescence line 200 in quantitative/qualitative analysis.

First, a light source is irradiated to the standard tray comprising the luminescence part 500 formed of the above-described standard material composition. In this case, the light source may be an external light source or a light source equipped in the analysis equipment, and its wavelength may be ultraviolet (blue light, <420 nm).

Next, whether the fluorescence intensity value of the luminescence part 500 emitted by the irradiated light source falls within a range of standard fluorescence intensity values input to an optical part of the bio-analysis equipment is determined. That is, the fluorescence signal emitted from the luminescence part 500 equipped in the standard tray is received by the optical part of the bio-analysis equipment, and whether the intensity of the received fluorescence signal falls within the range of the standard fluorescence signal intensities input (set) to the optical part is determined by the software of the optical part. Herein, the range of the standard fluorescence signal intensity values input to the optical part may be determined based on a numerical value according to quantum yields or photoluminescence that may represent a bio sample to be analyzed.

Next, the verification of the bio-analysis equipment may be performed through the process of first correcting the range of the standard fluorescence intensity values input to the optical part so that the fluorescence intensity value falls within the range of the standard fluorescence intensity values by the determination. Herein, when it is confirmed that the fluorescence intensity value of the luminescence part 500 falls within the range of the standard emission intensity values input to the optical part in the determination process, the first correction may be omitted. In addition, the first correction may be made by applying a standard strip comprising the luminescence line 200 instead of a standard tray comprising the luminescence part 500.

The method of verifying a bio-analysis equipment according to the present invention may further perform the process of secondarily correcting the standard fluorescence intensity values input to the optical part through the standard strip comprising one or more luminescence lines 200 formed of the above-described standard material composition. That is, a light source is irradiated to the standard strip comprising one or more luminescence lines 200, and whether the fluorescence intensity value of the luminescence line 200 emitted by the irradiated light source falls within the first corrected standard fluorescence intensity values set to the optical part of the bio-analysis equipment is determined. When it does not fall within the set standard fluorescence intensity values (first corrected standard fluorescence intensity values), the standard fluorescence intensity values set to the optical part of the bio-analysis equipment are secondarily corrected.

As an example, the correction of the optical part of the bio-analysis equipment through the standard strip comprising the luminescence line 200 may be performed by applying the correlation coefficient (c) as shown in FIG. 10 to the correction. That is, if the standard fluorescence intensity values input to the optical part of the bio-analysis equipment are analyzed and formulated through the standard strip prepared to have a fluorescence intensity value according to the equation $Y_0=a_0X+b_0$, the equation $Y_1=a_1X+b_1$ may be obtained. Herein, if the correlation coefficient (c) of $Y_0$ and $Y_1$ is obtained and is applied to $Y_1$, the corrected equation $Y_1'=c(a_1X+b_1)$ may be obtained. By correcting the error (deviation) of the optical part through the corrected equation $Y_1'=c(a_1X+b_1)$, the present invention may ensure that each bio-analysis equipment has the same fluorescence intensity value of the standard strip.

The first and/or second correction in the present invention is performed every predetermined period (1 month to 6 months) so that the verification process of the bio-analysis equipment may be updated.

In this way, since the present invention verifies (corrects) the bio-analysis equipment through the first and/or secondary correction process, the analysis error (deviation) of the bio-analysis equipment may be further minimized, and due to this, the analysis accuracy of the bio-analysis equipment may be increased.

The bio-analysis equipment in the present invention is not particularly limited as long as it is a bio-analysis equipment that has an optical part and in which software capable of analyzing the fluorescence intensity values is programmed, and may specifically include a mobile phone, a bio-reader, and the like. In addition, the error of the optical part of the bio-analysis equipment in the present invention may mean an error caused between the optical parts (CCD, CMOS) themselves of each bio-analysis equipment, an error caused by the operating environment of the optical part (illuminance of the surrounding environment), an error caused by the light source (UV), and the like, and the present invention may increase the analysis accuracy of the bio-analysis equipment by verifying (correcting) these errors.

Hereinafter, the present invention will be described in more detail by Examples. However, the following Examples are only for illustrating the present invention, it will be apparent to those skilled in the art that various changes and modifications may be made within the category and the scope of the technical spirit of the present invention, and the scope of the present invention is not limited thereto.

EXAMPLE 1

Quantum dot particles (CdSe/ZnS, 10 nm) coated with oleic acid were added and mixed to polyester resin, aromatic hydrocarbon-based solvent and additives (antifoaming agent, dispersion stabilizer), and then the process of adding a curing agent was performed to prepare a standard material composition. At this time, the quantum dot particles were added so as to be 5 parts by weight based on 100 parts by weight of the composition.

EXAMPLE 2

A standard material composition was prepared through the same process as in Example 1, except that the quantum dot particles were added in an amount of 10 parts by weight based on 100 parts by weight of the composition.

EXAMPLE 3

A standard material composition was prepared through the same process as in Example 1, except that the quantum dot particles were added in an amount of 20 parts by weight based on 100 parts by weight of the composition.

EXAMPLE 4

1) Preparation of Quantum Dot-Containing Nanoparticles

100 µl of 1% (v/v) mercaptopropyltrimethoxysilane (MPTMS) was added to the core part made of silica particles having a diameter of 120 nm (10 mg/ml), and a thiol group was introduced on the surface of the silica particles by stirring at 25° C. for 12 hours.

Next, 4 mg of quantum dot particles (CdSe/ZnS, 100 mg/ml) on which the process of coating with an oleic acid (hydrophobic) was performed were added to the thiol group-introduced silica particles, and the quantum dot particles were bonded to the thiol groups of the silica particles by vigorously stirring with a vortex. Then, 8 ml of dichloromethane, which is a hydrophobic solvent, was further added thereto, and stirred for 10 minutes to further bind unbound quantum dot particles. Then, 100 µl of mercaptopropyltriethoxysilane (MPTES) was added thereto and stirred for 15 minutes, and then 100 µl of 25% aqueous ammonia ($NH_4OH$(aq)) as a base was added and stirred for 3 hours to form a quantum dot part having a structure in which three quantum dot-embedded layers were stacked.

Next, the nanoparticle in which the core part and the quantum dot part were formed was washed with ethanol 3 times, and then 100 µl of tetraethyl orthosilicate and 25% aqueous ammonia were added thereto and stirred at 400 rpm for 20 hours to form a shell part. Thereafter, a three-time washing process with ethanol was performed to produce quantum dot-containing nanoparticle 1 comprising a silica core part; a quantum dot part in which three quantum dot-embedded layers were stacked; and a silica shell part.

2) Preparation of Standard Material Compositions

A standard material composition was prepared through the same process as in Example 1, except that quantum dot-containing nanoparticle 1 prepared through the above process was used instead of the quantum dot particles.

EXAMPLE 5

1) Preparation of Quantum Dot-Containing Nanoparticles

100 μl of 1% (v/v) mercaptopropyltrimethoxysilane (MPTMS) was added to the core part made of silica particles having a diameter of 120 nm (10 mg/ml), and a thiol group was introduced on the surface of the silica particles by stirring at 25° C. for 12 hours.

Next, 4 mg of quantum dot particles (CdSe/ZnS, 100 mg/ml) on which the process of coating with an oleic acid (hydrophobic) was performed were added to the thiol group-introduced silica particles, and the quantum dot particles were bonded to the thiol groups of the silica particles by vigorously stirring with a vortex. Then, 8 ml of dichloromethane, which is a hydrophobic solvent, was further added thereto, and stirred for 10 minutes to further bind unbound quantum dot particles.

Next, 150 μl of a carbon supporter (molecular weight of 1000 g/mol) having each of maleimide group and a triethoxysilane group bonded to both ends and having a main skeleton of polyethylene glycol was added thereto and stirred for 15 minutes, followed by 100 μl of mercaptopropyltriethoxysilane (MPTES) was added thereto and stirred for 15 minutes, and then 100 μl of 25% aqueous ammonia ($NH_4OH(aq)$) as a base was added thereto and stirred for 3 hours to bind a carbon supporter to the surface of the core part while forming a quantum dot part having a structure in which three quantum dot-embedded layers were stacked.

Next, the nanoparticles to which the core part, the quantum dot part, and the carbon supporter were bonded, were washed with ethanol 3 times, and then 100 μl of tetraethyl orthosilicate and 25% aqueous ammonia were added thereto and stirred at 400 rpm for 20 hours to form a support part and a shell part. Thereafter, a three-time washing process with ethanol was performed to produce quantum dot-containing nanoparticle 2 comprising a silica core part; a quantum dot part in which three quantum dot-embedded layers were stacked; a carbon support part; and a silica shell part.

2) Preparation of Standard Material Compositions

A standard material composition was prepared through the same process as in Example 1, except that quantum dot-containing nanoparticle 2 prepared through the above process was used instead of the quantum dot particles.

Preparative Example 1

A standard strip was prepared from each of standard material compositions prepared in Examples 1 to 3 (applied to the process of FIG. 6). Specifically, each of the standard material compositions prepared in Examples 1 to 3 is applied on an optical film (Optics film), covered with a cover film, and then subjected to a curing process to produce three QD films having different quantum dot concentrations (8×300 nm), respectively. Then, each prepared QD film was attached to the PVC Backing Card according to the line position of the PVC Backing Card (60×300 nm), patterned Black Tape (60×300 nm) was placed and attached on the PVC Backing Card so that the three QD film lines are exposed, thereby produce an uncut Standard Card. Next, the prepared standard card was cut to prepare a standard strip.

Experimental Example 1

After the standard strip prepared in Preparative Example 1 was mounted in a bio kit, UV light was irradiated to visually check the color of the quantum dot luminescence line, and then analyzed with a bio-only reader. The results of visual confirmation and reader analysis are shown in FIG. 11.

Referring to FIG. 11, only the signal of first line A was visually confirmed, but when analyzed with a reader, it could be seen that both line B and line C were confirmed along with line A. Using the fluorescence intensity values of the three lines confirmed in this way, correction of the optical part and light source of the bio-analysis equipment could be performed through the verification process of the bio-analysis equipment according to the present invention (through the equation correction process of FIG. 10).

The invention claimed is:

1. A standard material composition for verifying a bio-analysis equipment, comprising quantum dot-containing nanoparticles
wherein,
the quantum dot-containing nanoparticle comprises:
a core part;
a quantum dot part bound to a surface of the core part; and
a shell part for protecting the core part and the quantum dot part,
the quantum dot part comprises a first quantum dot-embedded layer and a second quantum dot-embedded layer,
the first quantum dot-embedded layer directly contacts and encloses the surface of the core part, and
a second quantum dot-embedded layer encloses the first quantum dot-embedded layer.

2. The standard material composition for verifying a bio-analysis equipment according to claim 1, wherein the shell part comprises a plurality of silica shell layers.

3. The standard material composition for verifying a bio-analysis equipment according to claim 1, wherein the quantum dot-containing nanoparticle further comprises a support part for supporting the binding of the core part and the shell part.

4. A standard strip comprising one or more luminescence lines formed of the standard material composition for verifying a bio-analysis equipment according to claim 1.

5. The standard strip according to claim 4, wherein the luminescence line is equipped in plurality, and the concentration of quantum dots is different between a plurality of luminescence lines.

6. The standard strip according to claim 4, wherein the luminescence line is equipped in plurality, and a fluorescence signal intensity is different between a plurality of luminescence lines.

7. A standard tray comprising a luminescence part formed of the standard material composition for verifying a bio-analysis equipment according to claim 1.

* * * * *